ns06528006B1

(12) United States Patent
Jansen

(10) Patent No.: US 6,528,006 B1
(45) Date of Patent: Mar. 4, 2003

(54) METHOD OF MACHINING PREFORMED PLASTIC FILM BY SEPARATION AND/OR ABLATION

(75) Inventor: Josef Jansen, Köln (DE)

(73) Assignee: Adiam Life Science AG, Erkelenz (DE)

( * ) Notice: Subject to any disclaimer, the term of this patent is extended or adjusted under 35 U.S.C. 154(b) by 0 days.

(21) Appl. No.: 09/555,392

(22) PCT Filed: Dec. 14, 1998

(86) PCT No.: PCT/DE98/03706

§ 371 (c)(1),
(2), (4) Date: May 26, 2000

(87) PCT Pub. No.: WO99/30884

PCT Pub. Date: Jun. 24, 1999

(30) Foreign Application Priority Data

Dec. 16, 1997 (DE) .......................................... 197 55 738

(51) Int. Cl.⁷ .............................................. B23K 26/36
(52) U.S. Cl. ...................... 264/400; 264/40.1; 264/129; 264/134; 264/139; 264/153; 264/233; 264/344; 264/482; 219/121.62; 219/121.67; 219/121.68; 219/121.69; 219/121.85; 427/596
(58) Field of Search ................. 264/400, 153, 264/40.1, 129, 134, 139, 233, 344; 219/121.67, 121.72, 121.73, 121.62, 121.85, 121.68–121.69; 427/596

(56) References Cited

U.S. PATENT DOCUMENTS

| 3,790,071 A | * | 2/1974 | Estephanian ................. 234/1 |
| 4,222,126 A | * | 9/1980 | Boretos et al. ................. 3/1.5 |
| 4,473,423 A | * | 9/1984 | Kolff ........................... 156/245 |
| 4,842,782 A | * | 6/1989 | Portney et al. ............... 264/1.4 |
| 4,851,061 A | * | 7/1989 | Sorkoram ..................... 156/63 |
| 5,128,170 A | * | 7/1992 | Matsuda et al. ............... 427/2 |
| 5,211,805 A | * | 5/1993 | Srinivasan .................. 156/643 |
| 5,240,553 A |   | 8/1993 | Jones |
| 5,376,113 A | * | 12/1994 | Jansen et al. ................. 623/2 |
| 5,397,347 A |   | 3/1995 | Cuilleron et al. |
| 5,443,501 A | * | 8/1995 | Barmada ....................... 623/2 |
| 5,486,546 A | * | 1/1996 | Mathiesen et al. .......... 522/165 |
| 5,554,184 A | * | 9/1996 | Machiraju .................... 623/2 |
| 5,736,999 A | * | 4/1998 | Aoki ........................... 347/47 |
| 5,792,411 A | * | 8/1998 | Morris et al. ............... 264/400 |
| 5,883,356 A | * | 3/1999 | Bauer et al. ........... 219/121.62 |
| 5,935,506 A | * | 8/1999 | Schmitz et al. ............. 264/400 |

FOREIGN PATENT DOCUMENTS

| DE | 32 48 560 A1 | 7/1984 |
| DE | 37 34 656 A1 | 4/1988 |
| DE | 691 02 325 T2 | 9/1991 |
| DE | 40 13 163 A1 | 10/1991 |
| DE | 41 33 620 C1 | 4/1993 |
| DE | 195 28 215 A1 | 2/1997 |
| DE | 195 31 590 A1 | 3/1997 |
| JP | 05-016246 | * 1/1993 |
| WO | WO 95/15254 | 6/1995 |

OTHER PUBLICATIONS

Einsatzmöglichkeiten Des Laser—Und Des Wasserstrahl-schneidverfahren . . . by B.K. Engenmann (Kunststoffe 71 (1981) 9.
Laserbeschriften Von Kunststoffformteilen by V. Pfeufer et al. (Laser Praxis Jun. 1989.
Bohren Von Leiterplatten Mit Excimerlasern by F. Bachmann et al. (Laser Praxis Jun. 1989).
ExcimerLaser–Anwendungen in Der Chemie–Und Kunststoffindustrie by P. Holzer et al. (Kunstoffe 79 (1989)6.

* cited by examiner

*Primary Examiner*—Stefan Staicovici
(74) *Attorney, Agent, or Firm*—Herbert Dubno

(57) ABSTRACT

The invention relates to a method of producing plastic film having a predefinable outline and/or even or uneven thickness, by machining preformed plastic film for separation and/or ablation. The method is used especially for producing flexible flaps for artificial heart valves. To produce a film having local variations in thickness and smooth edges where the piece of film has been cut, the invention provides for the plastic film to be separated and/or for specific areas to be ablated to the desired thickness by means of a laser beam.

18 Claims, No Drawings

METHOD OF MACHINING PREFORMED PLASTIC FILM BY SEPARATION AND/OR ABLATION

CROSS REFERENCE TO RELATED APPLICATIONS

This application is a national stage of PCT/DE 98/03706 filed Dec. 14, 1998 and based upon German national application 197 55 738.4 filed Dec. 16, 1997 under the International Convention.

FIELD OF THE INVENTION

The present invention relates to a method for producing synthetic resin films with a predetermined contour and/or a uniform or nonuniform thickness distribution by a separation and/or ablation machining of preformed synthetic resin films, especially for the production of flexible leaflets (e.g. cusps, flaps] for artificial heart valves.

BACKGROUND OF THE INVENTION

Thin plastic films can be produced by various processes as, for example, injection molding, deep drawing, dip molding or casting. To the extent that the films can have a thickness of 500 $\mu$m and more, and the thickness distribution over the entire foil area is not significant or has only a subordinated significance, as a rule no after treatment of the foil is required over the area thereof and the foil can be stamped to produce the desired contour. It is different, however, when for such synthetic resin foils, a reproducible adjustable uniform thickness or thickness variations are desired in a locally defined manner which can be in a range of 30 $\mu$m to 500 $\mu$m.

Prosthetic heart valves are comprised of a support housing with a base ring carrying at least two posts extending substantially in the axial direction of the ring and which are connected by an arcuate wall structure serving for fastening of the flexible leaflets or cusps as has been described, for example, in DE 38 34 545 C2. The three leaflets there shown for an aortic heart valve insure the closing and opening, whereby the leaflets at their free edges lie against one another with formation of an overlapping region in the closed state. The known construction and that described in DE 42 22 610 A1 tend to closely resemble the natural aortic valve which has the connection line of the leaflet or cusp with the natural aortic root approximately formed by the intersection of a cylinder with the aorta. At this region, the connecting line closes the upstream side of the commissure, at which the lines or the leaflets contact. The commissures prevent a breakdown of the leaflets and serve in combination with the leaflet overlap regions to brace the leaflets. From the foregoing, it is apparent that the leaflets connected with the stent, whether they form a heart valve with three or two leaflets are differently stressed at different locations, whereby depending upon the type and magnitude of the mechanical stress, the respective thicknesses should be locally adjusted. Apart from regions of greater thickness, there thus must be regions of thicknesses below 50 $\mu$m.

Apart from the desired thickness distributions, it is advantageous to obtain the smoothest possible and most homogeneous-free leaflet edge. Both the optimum thickness distribution and also the smooth leaflet edge influence to a significant degree of durability of the prosthesis since the leaflets must be capable of withstanding billions of bending load alternations. Injection and dip casting processes are indeed basically used to produce a foil with local differences in thickness although these processes cannot provide the desired degree of reproducibility of the dimensions and also cannot provide fabrication thicknesses below 100 $\mu$m. Such thicknesses can only be obtained with extremely high apparatus costs. The quality of the free leaflet edges is insufficient when the cusps are made by these processes.

OBJECT OF THE INVENTION

It is thus the object of the present invention to provide a process of the initially described type which permits a foil to be obtained with extremely small thicknesses and with locally different thickness distributions as well as with a smooth closure edge of the cut foil piece.

SUMMARY OF THE INVENTION

These objects are achieved with a method which is characterized in accordance with the invention in that the synthetic resin foil is separated by means of a laser beam bundle along the predetermined contour and/or is subjected to ablation in an area-wise manner until the respective desired thickness dimension is obtained.

Surprisingly, it has been found that the area-wise ablation and separation can be carried out reproducibly with the requisite precision while the synthetic resin surface is locally melted at respective laser burn spots and the melted material vaporized. The differences in the separation and area-wise ablation by means of a laser lies only in the penetration depth or machining depth, whereby the separation or cutout of the desired synthetic resin foil contour is effected by forming a groove with growing depth. The laser and the optics associated therewith form a machining tool which does not come into contact with the workpiece so that no wear is generated. Via corresponding servomotors, exact guidance of the laser beam bundle is possible. The process of the invention thereby has the advantage that, from the viewpoint of the synthetic resin foil thickness dimension as produced by injection, dip casting or spraying, there are no requirements from the point of view of the desired thickness distribution since the foil can be directly subjected to a material removal process. This means in addition that initially there is a significant simplification in the process technology since thicker foils can be produced which are later correspondingly profiled and contoured.

SPECIFIC DESCRIPTION

Preferably the synthetic resin foil is sensed by a scanning-like procedure whereby the instantaneous thickness is measured pointwise and stored and thereafter the stored values are utilized to generate the setting parameters for the laser required for the separation and/or areawise ablation, these parameters being, for example, the energy density, the pulse rate and the effective duration. These features are based upon the thought that initially a synthetic resin foil produced by the optional shaping process is measured from the viewpoint of its thickness distribution and thereafter by comparison with a setpoint thickness distribution, the variation from place to place is determined and the degree to which the surface layer must be ablated is determined.

In a corresponding manner, via the pulse rate, the laser burn spot duration and energy density, the permissible depth of penetration is obtained such that reduced penetration depths which lie below the depth to be ablated require a longer application time of the laser beam bundle on the workpiece surface or a plurality of sweeps over this piece. The areal extent of the effect of the laser beam bundle on the workpiece surface is oriented based upon the gradient with which the thickness distribution along the profile is to be changed. A greater thickness change for a shorter stretch requires a smaller laser burn point in terms of the areal extent than does a laser variation in the thickness reduction.

Preferably for the separation and/or area-wise ablation of the workpiece, an eximer laser, preferably an ArF laser, a KrCl laser or a KrF laser is used. These lasers, operating in the UV range are pulsed lasers in which the pulse rate and the pulse count, the energy density and the speed can be adjusted to vary the degree of ablation of the synthetic resin surface.

To reduce reactions during laser treatment of the molten surface with the ambient environment or a deposit of solid particles (dust) the synthetic resin film surface treatment is preferably carried out under a pressure of 10 Pa to $10^{-1}$ Pa, preferably at 1 Pa. The corresponding vacuum serves simultaneously for sucking away from above the plastic surface the vapor pressure resulting from the melting.

According to a further feature of the invention, the surface treatment is carried out under an $O_2$ or a protective gas atmosphere which is comprised preferably of nitrogen and/or helium. Preferably the laser beam bundle energy density is between 0.3 and 1.2 J/cm$^2$. As optimal pulse frequencies, those between 20 to 400 Hz, preferably 20 Hz to 150 Hz, have proved to be desirable. To the extent excessive thickness gradients along a specific film profile are to be obtained, as for example with high radii of curvature of the free-form areas of cusps in artificial heart valves, diameters of irradiated circular areas between 80 to 600 $\mu$m have proved to be satisfactory for rectangular irradiated surface elements with edge lengths of a maximum of 800 $\mu$m.

According to a further feature of the invention, the laser beam bundle for area-wise ablation is guided over the surface to be measured in a meander pattern whereby the passes resulting from the guiding of the laser beam bundle are partly overlapped to a slight extent. Because of this feature, the energy deposit of the last beam bundle is anticipated to be less toward the edges of the pass with the consequence that in the edge regions of each pass the ablation of the workpiece surface is reduced. Because of the stripwise overlapping in these edge regions, whereby the next pass edge region runs over the edge region of the previous pass, ablation of the desired thickness is ensured.

Preferably the one or multilayer plastic film, which advantageously is comprised of polyurethane, is produced by injection molding, deep drawing, dip molding and/or spraying on a mold. The separation of the desired foil piece can be effected while the foil lies on the mold. The mold is not damaged thereby and can be used a multiplicity of times.

According to a further feature of the invention, the plastic foil before machining is coated by means of a laser beam bundle with a protective layer which after laser machining is again removed. The material removed by means of the laser beam bundle from the interface or from the surface of the plastic film is vaporized. The material vapor thus produced is composed of a variety of components from fractions of the macro molecules to particles in the micrometer range. To prevent such particles or other deposits from the vapor phase mainly as debris particles from depositing directly on the plastic film, the latter can be coated for the interim with a protective layer, for example by a dip or spray process. This protective layer can be removed with the debris after the machining so that the completed film contour and thickness is again obtained after removal of the protective layer. Preferably the protective layer is comprised of water-soluble material that can be easily washed away after laser treatment.

According to a further feature of the invention, the protective layer material is biocompatible, i.e. physiologically nonproblemmatical, so that any residues remaining even after flushing of the protective film can be decomposed by the human body without detriment. As protective layer materials, especially water soluble polymers with weight average molecular weights between 2000 and 150000 with film forming characteristics are suitable. Preferred polymers for this purpose are polyethyleneoxides, polyvinylalcohols, polyvinylpyrrolidones, polysaccharides, polylactides, polysodiumstyrenesulfonates and/or polyacrylic acids as well as mixtures of these substances. Also other water soluble, biocompatible and physiologically nonobjectionable further organic compounds will be self understood to be also within consideration.

In a concrete example, the cusps of an aorta heart valve are produced by the process according to the invention. The separating process of the invention allows the separation of the free cusp edges along a approximately optional space curve with a surfacewise ablation to establish locally predetermined cusp thicknesses. Thus in the region of the so-called Nodulus Arantii, where the three cusps meet upon valve closure, a comparatively thin thickness is produced on the one hand to ensure reliable closure of the valve and on the other hand to keep the bending stress to a minimum.

To produce the polyurethane cusp, a mold is used which can be immersed a multiplicity of times until the hardened layer on the immersion mold has a thickness which at every location is at least as great as the locally desired thickness. Both the separation, i.e. the cutout of the desired cusp contour as well as the surface ablation of the surface regions for targeted thickness adjustment are carried out by means of ArF laser with a wavelength of 193 nm. The discharge volume is limited by diaphragms so that an isotropic beam with reduced divergence is emitted. While this limits the pulse energy (for separation of the cusp) to about 10 mJ, the beam quality is so enhanced that with use of a simple planoconvex lens, with a focal length of 50 mm, a fine cut can be achieved. The plastic film is then placed in a vacuum chamber which is covered with a suprasil window. The laser beam or laser beam bundle and through a machine microscope and with the aid of the aforementioned lens, a circular spot with a diameter between 90 $\mu$m and 600 $\mu$m was imaged through the window on the plastic film. The chamber was moved relative to the laser beam with a controlled stepping motor at a constant speed. In the chamber, the plastic film was machined under a superatmospheric pressure of $10^2$ Pa and maintained by further pumping. Alternatively, nitrogen, oxygen or helium was introduced at a pressure between 1 and $10^4$ Pa. In part, the separating operation was carried out also under normal pressure in air. The distance between the plastic film and the mentioned supersil window should not be selected to be too small since at a spacing of about 20 mm and a pressure less than $10^3$ Pa, a yellowish-brown deposit can be observed on the window. This results from deposition of the vapors and can give rise to fluctuating transmission of light through the window between 30 and 65%, even in the case in which the laser beam burns its passage free therethrough. The cutting speed depends substantially upon the ablation rate, i.e. the ablation depth per pulse which can be between 0.05 $\mu$m/pulse to 1 $\mu$m/pulse depending upon the energy density used between 0.55 J/cm$^2$. The pulse rate was varied between 30 Hz, 100 Hz and 150 Hz; with the aid of a round diaphragm, beam diameters of values of 90 $\mu$m, 225 $\mu$m and 600 $\mu$m were set.

The material which was removed from the cutting kerf from the plastic film by the laser beam bundle flows with a preferred direction perpendicular to the surface. The vaporized material is composed of various components from fractions of the macromolecule to particles in a μm size range. The portion of these particles deposited adjacent the cutting kerf and appear as a brownish deposit which, under the microscope, can be recognized as an accumulation of particles (so-called debris). The typical particle size amounts to about 200 nm. From this it appears that the environmental conditions can affect the quantity and nature of the deposits. The best results can be obtained in vacuum (less than $10^4$ Pa) in which the material flows off unhindered. It is also advantageous to use oxygen or helium as a flushing gas.

As has already been noted previously, in a further example, the plastic film used was coated prior to the treatment with the laser beam bundle with a water soluble and biocompatible protective layer. As protective layers, polyethyleneoxides, polyvinylalcohols, polyvinylpyrrolidones, polysaccharides, polylactides, polysodiumstyrenesulfonates, or polyacrylic acids or mixtures of these substances were used.

The thickness of these layers amounted to only several micrometers (preferably up to a maximum of 10 μm) since the protective layer serves only to capture the particle deposits, i.e. to prevent these particle deposits from depositing upon the film itself. After the cutting or surface treatment of the plastic film, the protective film, which is water soluble, is washed away, thereby simultaneously removing the particles. In this manner, the finished thickness or plastic film surface is restored.

The cuts can be achieved in a single working pass or with two or more passes of a trace which simultaneously forms the separation line.

For surface ablation of the plastic surface, a laser beam bundle is used whose area on the plastic surface amounts to about 400×800 μm. The laser beam bundle is moved parallel to its edge over the plastic surface film, whereby the laser is operated with a fixed pulse frequency. After a predetermined stretch, the laser beam is shifted to the side and moved back parallel to the previous pass whereby the areas overlap in the respective passes at their edges. At the direction reversal point, the laser has its pulse frequency synchronized to the displacement speed. As a result of the meander-shaped passage of a multiplicity of parallel traces, the ablation is stepped over the entire plastic surface. The parameters: energy density, pulse frequency and pulse count are so varied, depending upon the previous thickness measurement scanned into the system that at each point the polyurethane foil is machined to the desired thickness. Independent of the pulse count, the system is operated at a 20 Hz pulse rate at an energy density of 0.17 to 0.93 J/cm$^2$. In a further series, pulse rates up to 80 Hz with energy densities between 0.37 to 1.1 J/cm$^2$ can be used.

Tests have shown that the development of bubbles, tapers or grooves can be used at energy densities of more than 0.2 J/cm$^2$, preferably more than 0.4 J/cm$^2$. The pulse rate is preferably below 80 Hz.

With the aforementioned process, it is possible to locally produce a reduced thickness of less than 50 μm. While both the separation of the polyurethane foil and also the surface ablation thereof can be carried out with a round or a rectangular laser beam bundle, a round bundle is preferred.

The thickness distribution of a cusp is preferably so selected that the thickness distribution corresponds to that of a natural cusp. Such a thickness distribution is described for aortic cusps in, for example, Richard E. Clark et al, "Leaflet Prosthetic Valves, Cardiovascular Diseases, Vol. 1, No. 3, 1974, page 437, and lies between 0.25 mm and 1.5 mm. For the harder plastic films used, for example of polyurethane, the plastic cusp thickness distribution corresponds to between 50 and 250 μm.

I claim:

1. A method of making single or multilayer plastic film with a predetermined contour and/or a uniform or nonuniform thickness distribution by separating and/or ablating machining of prefabricated plastic film, in the production of flexible cusps for artificial heart valves, wherein the prefabricated plastic film is separated along the predetermined contour by means of a laser beam bundle and/or is areawise ablated to the respective desired thickness measurement by means of a laser beam bundle, the single or multilayer plastic film is made from polyurethane by injection molding, deep drawing, immersion and/or spraying on a form and then is ablated areawise and/or cut out and, before ablating machining, the prefabricated plastic film is coated by means of a laser beam bundle with a protective layer which is removed after ablating machining, wherein the protective layer is comprised of water soluble material which is washed away after the ablating machining and is biocompatible.

2. A method of making single or multilayer plastic film with a predetermined contour and/or a uniform or nonuniform thickness distribution by separating and/or ablating machining of prefabricated plastic film, in the production of flexible cusps for artificial heart valves, wherein the prefabricated plastic film is separated along the predetermined contour by means of a laser beam bundle and/or is areawise ablated to the respective desired thickness measurement by means of a laser beam bundle, the single or multilayer plastic film is made from polyurethane by injection molding, deep drawing, immersion and/or spraying on a form and then is ablated areawise and/or cut out and, before ablating machining, the prefabricated plastic film is coated by means of a laser beam bundle with a protective layer which is removed after the ablating machining, wherein the protective layer is comprised of water soluble polymers with a weight average molecular weight between 2,000 and 150,000.

3. The method according to claim 2 wherein the protective layer is composed of polyethyleneoxides, polyvinylalcohols, polyvinylpyrrolidones, polysaccharides, polylactides, polysodiumstyrenesulfates and/or polyacrylic acids or mixtures thereof.

4. A method of making an artificial leaflet for a heart valve, comprising the steps of:
    (a) forming a synthetic resin film compatible for use in a heart valve;
    (b) cutting out, with a laser beam bundle, an artificial leaflet blank from said synthetic resin foil along a predetermined contour; and
    (c) selectively sweeping a laser beam bundle over a surface of said artificial leaflet blank to selectively remove material therefrom and impart predetermined thicknesses to parts of said artificial leaflet blank and form locally different thickness distributions, thereby producing the artificial leaflet for said heart valve.

5. The method defined in claim 4, further comprising the steps of:
    scanning said blank to determine thicknesses of said film at different locations;
    comparing stored thickness values for said film with measured thicknesses; and
    controlling at least one parameter of said laser beam bundle selected from the group consisting of an energy density of laser treatment of said surface, laser pulse rate, and effective duration of laser treatment in response to comparison of stored thickness values with measured thicknesses.

6. The method defined in claim 4 wherein said laser beam bundle is formed by an ArF, KrCl or KrF eximer laser.

7. The method defined in claim 4 wherein the cutting of said film and the removal of material from said surface are carried out at a pressure of 10 Pa to $10^{-1}$ Pa.

8. The method defined in claim 7 wherein said pressure is 1 Pa.

9. The method defined in claim 4 wherein the cutting of said film and the removal of material from said surface are carried out under an $O_2$ or a protective gas atmosphere of nitrogen or helium.

10. A The method defined in claim 4 wherein the cutting of said film and the removal of material from said surface are carried out with a laser beam bundle energy density between 0.3 and 1.2 $J/cm^2$.

11. The method defined in claim 4 wherein the cutting of said film and the removal of material from said surface are carried out with a laser beam bundle pulse frequency between 20 to 150 Hz.

12. The method defined in claim 4 wherein the cutting of said film and the removal of material from said surface are carried out with a laser beam bundle treatment area which is circular with a diameter of 80 to 600 µm or is rectangular with a side length of at most 800 µm.

13. The method defined in claim 4 wherein the removal of material from said surface is carried out by moving laser beam bundle in a meander pattern over the surface with slight overlapping of passes of the laser beam bundle.

14. The method defined in claim 4 wherein said film has one or more layers and is made from polyurethane by injection molding, deep drawing, immersion or spraying on a form.

15. The method defined in claim 4 wherein the film, before cutting or material removal by said laser beam bundle, is coated with a protective layer and which is removed after cutting or material removal by said laser beam bundle.

16. The method defined in claim 15 wherein said protective layer is comprised of water-soluble material which is washed away after cutting or material removal by said laser beam bundle or is bio-compatible.

17. The method defined in claim 16 wherein the protective layer is comprised of water-soluble polymers with a weight average molecular weight between 2000 and 150000.

18. The method defined in claim 17 wherein the protective layer is composed of polyethyleneoxides, polyvinylalcohols, polyvinylpyrrolidones, polysaccharides, polylactides, polysodium-styrenesulfates or polyacrylic acids or mixtures thereof.

* * * * *